US007776818B2

(12) United States Patent
Beardsley (10) Patent No.: US 7,776,818 B2
(45) Date of Patent: Aug. 17, 2010

(54) METHODS TO TREAT T-CELL DISORDERS USING TISF

(75) Inventor: Terry Raymond Beardsley, Temecula, CA (US)

(73) Assignee: S-Cell Biosciences, Inc., Murrieta, CA (US)

( * ) Notice: Subject to any disclaimer, the term of this patent is extended or adjusted under 35 U.S.C. 154(b) by 217 days.

(21) Appl. No.: 11/529,937

(22) Filed: Sep. 29, 2006

(65) Prior Publication Data

US 2007/0087968 A1    Apr. 19, 2007

Related U.S. Application Data

(60) Provisional application No. 60/722,847, filed on Sep. 29, 2005.

(51) Int. Cl.
*A01N 37/18* (2006.01)
(52) U.S. Cl. ............................ 514/2; 514/8
(58) Field of Classification Search .................. None
See application file for complete search history.

(56) References Cited

U.S. PATENT DOCUMENTS

| 5,616,554 A | 4/1997 | Beardsley |
| 2002/0086049 A1 | 7/2002 | Bolton et al. |
| 2005/0107300 A1 | 5/2005 | Beardsley et al. |
| 2007/0087968 A1 | 4/2007 | Beardsley |

FOREIGN PATENT DOCUMENTS

WO    WO-2005/025594    3/2005

OTHER PUBLICATIONS

Williemzie et al, Leukemia & Lymphoma, 2003, 44:S49-S54.*
Rodriguex-Abreu et al, Hematol Oncol, 2008 26:8-20.*
Cheson et al, Sem in Oncol, 2007, 34:S3-S7.*
Beardsley et al., PNAS USA (1983) 80:6005.
Beutler and Bazzoni, Blood Cells, Molecules, and Diseases (1998) 24(10):216-230.
Badley et al., Blood (2000) 96(9):2951-2964.
Burger et al., Exp. Dermatol. (2004) 13:406-412.
Cleveland et al., J. Biol. Chem. (1977) 252(3):1102-1106.
Devlin, (ed.), Textbook of Biochemistry with Clinical Correlations, 5th ed., (2002) Wiley-Liss, p. 23.
Knazek and Gullino, Tissue Culture Methods and Applications, Chapter 7, Kruse and Patterson (eds.), Academic Press, NY (1973) p. 321.
Thompson, Science (1995) 267:1456-1461.
International Search Report and Written Opinion for PCT/US06/38028, mailed Jul. 30, 2007, 4 pages.
Strayer et al., Journal of Immunology (1986) 137(11):3632-3638.
Supplementary European Search Report for EP 06 82 5240, issued Oct. 8, 2009, 6 pages.

* cited by examiner

*Primary Examiner*—Misook Yu
*Assistant Examiner*—Mark Halvorson
(74) *Attorney, Agent, or Firm*—Morrison & Foerster LLP (57) ABSTRACT

T4 Immune Stimulating Factor (TISF) selectively induces aberrant T-cells to initiate apoptosis. TISF and peptides that are related to TISF (TISF peptides) are therefore useful for the treatment of disorders characterized by aberrant production, development, or activity of T-cells or other cells of hematopoietic origin. This invention relates to methods of using TISF or a TISF peptide to treat such conditions, compositions containing TISF or a TISF peptide for use in such treatments, and use of TISF or a TISF peptide for the manufacture of pharmaceuticals.

6 Claims, 6 Drawing Sheets

|  | necrosis | angiogenese | Size |
|---|---|---|---|
| CTCL-1 | +++ | ++ | +++ |
| CTCL-2 | - | - | - |
| CTCL-3 | + | - | + |
| CTCL-4 | +++ | ++ | + |
| CTCL-5 | ++/+++ | +/++ | ++ |
| CTCL-6 | ++ | ++ | ++ |
| CTCL-7 | +++ | ++ | +++ |
| CTCL-8 | + | - | - |
| CTCL-9 | +++ | - | ++ |
| CTCL-10 | ++ | ++ | ++ | controls

|  | necrosis | angiogenese | Size |
|---|---|---|---|
| CTCL-11 | - | - | +++ |
| CTCL-12 | ++ | + | ++/+++ |
| CTCL-13 | no data | no data | no data |
| CTCL-14 | - | + | ++ |
| CTCL-15 | ++ | + | +++ |
| CTCL-16 | +++ | + | +++ |
| CTCL-17 | no data | no data | no data |
| CTCL-18 | (+) | + | + |
| CTCL-19 | (+) | + | + |
| CTCL-20 | (+) | + | + |

Histopathological grading (semiquantitative)

+ = mild occasional necrosis and angiogenesis

++ = moderate necrosis, multifokal, moderate angiogenesis

+++ = severe, partially confluent necrosis, tumor highly vascularized

++++= tumor totally dissolved relative size of tumor
+-++++= size of the tumor tissue was estimated, but is only not a real histometric or stereological assessment

Figure 6

Histology CTCL

1 The image revals neoplastic T-cells of the control group, with no signs of necrosis and a hight proliferative index. CTCL 14

2 identical to 1

3 Necrotic area of the CTCL-5 animal of the treatment group 5 increased angiogenesis and small hemorrhages in the treatment group. CTCL 6

Figure 7

METHODS TO TREAT T-CELL DISORDERS USING TISF

CROSS-REFERENCE TO RELATED APPLICATIONS

This application claims benefit of priority to U.S. Provisional Application Ser. No. 60/722,847, filed on Sep. 29, 2005, the contents of which are incorporated herein by reference.

BACKGROUND

Apoptosis is a genetically regulated mechanism for programmed cell death, which is important from embryogenesis throughout adult life. It eliminates cells that are not useful to the multicellular organism by mechanisms that are distinct from the mechanisms that kill cells due to injury, anoxia, etc. Apoptosis is initiated by a signal to the cell, which activates a cascade of reactions involving various protein factors and proteolytic enzymes. The very specialized proteases involved, called caspases, are normally present in proenzyme form, and are activated by a cleavage mechanism. They then hydrolyze specific proteins, which initiates disassembly of the cell. *Textbook of Biochemistry with Clinical Correlations*, $5^{th}$ ed., pg. 23 (Thomas M. Devlin, ed., Wiley-Liss (2002)).

Different types of cells have different receptors that can be stimulated to initiate apoptosis; the specificity of these receptors is obviously critical to the survival of an organism, because it determines which cells survive and which die. Dysfunctions in the apoptosis machinery are associated with a variety of disorders including immune disorders, inflammatory conditions, malignancies, neurodegenerative diseases, and viral infections that affect the immune system. Id. See also *TNF, Apoptosis and Autoimmunity. A Common Thread?*, B. Beutler and F. Bazzoni, *Blood Cells, Molecules, and Diseases*, 24(10), 216-30 (1998) (electronic journal, available online at http://www.scripps.edu/bcmd/).

Apoptosis has been described as a systematic process for eliminating unneeded or defective cells to maintain balance. C. B. Thompson, *Science*, vol. 267, 1456-61 (1995). Thus apoptosis provides a mechanism which could also be useful to eliminate defective cells such as malignancies if it could be selectively triggered in those cells. Tumor necrosis factor (TNF), a cytokine which selectively initiates apoptosis in tumor cells, demonstrated that treatment of cancer could in theory be accomplished with this approach, and efforts related to TNF continue, often focused on ways to control production of cytokines.

A substance referred to as T4 immune stimulating factor (TISF) has been identified and described recently due to its immune-stimulating activities. U.S. Pat. No. 5,616,554. TISF is alternatively referred to as Epithyme™ and as S-Celergin at times herein and in other references. It is one of a number of factors that have been described which stimulate various stages of CD4+ lymphocyte development. TISF stimulates a normally unresponsive population of cells at a later stage of the development process, while a different factor stimulating an earlier stage of the process is described, for example, in Beardsley, et al., *PNAS* 80: 6005 (1983).

TISF is a polypeptide that is typically glycosylated. It "stimulates, enhances or regulates cell-mediated immune responsiveness" by stimulating mature T-lymphocytes as described in U.S. Pat. No. 5,616,554. It is thus able to enhance the immune response of animals to infectious agents and to some malignancies. Id. In addition, TISF has been reported to promote hematopoiesis, or blood cell development, possibly by its ability to stimulate CD4+ lymphocytes. U.S. application Ser. No. 10/938,451. Thus in cats having feline immunodeficiency virus or feline leukemia virus infections, treatment with TISF increased lymphocyte counts, and also increased red blood cell, platelet and granulocyte levels. Id.

Cytokines, broadly defined, are cell-derived hormone-like peptides that regulate cellular replication, differentiation, or activation related to defense and/or repair of the host organism. Thus based on its activities described above, TISF may be considered a cytokine, like interferon, TNF, and the interleukins. However, as described in U.S. Pat. No. 5,616,554, TISF is distinct from the known cytokines.

Surprisingly in light of its ability to stimulate hematopoiesis, it has now been found that TISF is also capable of initiating apoptosis in some cell populations, including certain types of blood cells. In particular, it has been found that TISF selectively causes cell death or cessation of tissue growth in aberrant T-cells, such as lymphoma cells, lymphocytes that carry HIV virus, and leukemic cells. While reported to be capable of stimulating an immune response that could in theory target malignant cells, see U.S. Pat. No. 5,616,554, it is surprising to find that TISF can cause cell death selectively in compromised T-cells in the absence of any immune response, as demonstrated by in vitro experiments.

The present invention relates to methods of using TISF to treat disorders characterized by production, development, or activity of aberrant T-cells. Because it operates by a mechanism independent of the stimulation of the immune response previously associated with TISF, it provides methods to treat such conditions in immune-compromised individuals where a treatment relying on stimulation of the subject's immune response would not be expected to work well. For example, it is especially well suited to the treatment of subjects having an immune disorder such as HIV and treatment of subjects who are concurrently receiving immune-suppression drugs.

Each reference cited herein is incorporated by reference in its entirety. No citation of any document is an admission that such document constitutes prior art to this application.

BRIEF SUMMARY OF THE INVENTION

The present invention provides methods for treating disorders characterized by production, development, or activity of aberrant cells of hematopoietic origin, and especially of aberrant leukocytes or T-cells. While not limited by any theory of how the methods operate, the invention originated in the discovery that TISF stops growth of and induces apoptosis in aberrant T-cells. Aberrant T-cell disorders include those where T-cells have become malignant or infected with a virus. Apoptosis is selectively triggered in such T-cells by treatment with TISF or a peptide related to TISF (herein referred to as a TISF peptide). Thus TISF or TISF peptides and compositions comprising such peptides are useful for the treatment of these disorders, which include a variety of T-cell lymphomas like mycosis fungoides, T-cell leukemias, and some viral infections like HIV that are harbored by T-cells. Typically, the TISF is obtained in substantially pure form from a mammalian tissue or cell, as by culturing a mammalian cell followed by extracting the TISF or TISF peptide and using conventional methods to purify the TISF or TISF peptide. In certain embodiments, TISF is produced by a thymic cell culture, and TISF peptides are often prepared by modifications of TISF from such cultures, typically by selective proteolysis.

The invention also includes pharmaceutical compositions comprising TISF or a TISF peptide, preferably in substantially pure form, in combination with at least one pharmaceutically acceptable excipient. It further includes methods for the preparation of a medicament for the treatment of disorders characterized by aberrant production, development, or activity of T-cells or other cells of hematopoietic origin, where such medicament comprises TISF or a TISF peptide.

The invention also provides methods to induce apoptosis in an aberrant lymphocyte by contacting the aberrant lymphocyte with TISF or a TISF peptide. The lymphocyte may be contacted with TISF or a TISF peptide ex vivo or in vivo, and in many embodiments, the lymphocyte is contacted with TISF or a TISF peptide in vivo, often in a human or other mammal. The subject may be one diagnosed with a T-cell lymphoma such as those described herein, or with a T-cell leukemia, or it may be a subject diagnosed with HIV, wherein the aberrant hematopoietic cells are those containing HIV virus.

DETAILED DESCRIPTION OF THE INVENTION

TISF is described as a 50 kD protein with an isoelectric point of 6.5, which may be glycosylated. It is also sometimes referred to as S-Celergin, and a product referred to as "Thymic Protein A", which is a thymus cell culture extract, reportedly contains TISF. Methods for the production and isolation of TISF that are applicable to preparation of TISF from a mammalian species are described in U.S. Pat. No. 5,616,554.

As used herein, the term "TISF" refers to a protein having the physical and biological properties of a TISF proteinaceous substance as described in U.S. Pat. No. 5,616,554. The substance may be obtained for instance by isolation from thymic tissue of cells of a mammalian species such as bovine, ursine, equine, feline, canine, murine, or human. U.S. Pat. No. 5,616,554 provides methods for producing and characterizing TISF from a culture of thymus cells obtained from the appropriate mammalian species, and is incorporated herein by reference in its entirety.

As used herein the term "mammalian TISF" refers to a protein that has the physical and biological properties of TISF found in a mammalian species, without regard to how the protein was actually obtained. Thus, for example, the TISF obtained from a cell culture is included within the scope of the claims provided it has the same biological and physical properties as that found in a mammalian species. Similarly, "human TISF" refers to the peptide having the physical and biological properties of TISF found in humans, and is not limited to TISF that was obtained from a human.

As used herein, the term "TISF peptide" refers to a polypeptide or glycosylated polypeptide obtainable by partial hydrolysis or proteolysis of a protein referred to as TISF in U.S. Pat. No. 5,616,554, provided the material retains at least 20% of the activity of TISF from a mammalian species, as measured by the mouse xenograft model described herein.

TISF has been found to inhibit growth of aberrant cells of hematopoietic origin. These aberrant cells include cells that lack normal growth regulation means, and cells that are compromised by an infecting virus or detrimental mutation. TISF, and TISF peptides, inhibit the growth of such aberrant cells and thereby alleviate symptoms associated with the production, activity or development of such aberrant cells.

TISF has been shown to inhibit cell growth in a culture of lymphoma cells in a dose-dependent manner, as demonstrated by $^3$H-thymidine incorporation experiments. It was also shown to increase cell death rate among lymphocytes infected with the HIV virus. In such cells, TISF also slowed the production of virus. Furthermore, when cells of human myelomonocytic leukemia cell line K562 were treated with TISF, the level of apoptosis in that cell culture increased by more than two-fold over a control. By comparison, TISF exerted no effect on growth rate of the cells of a non-lymphoid malignant cell line, demonstrating that the effect on lymphoma cells is not a general cytotoxic effect, nor is it attributable to a systemic immune response induced by TISF.

Figure 1:
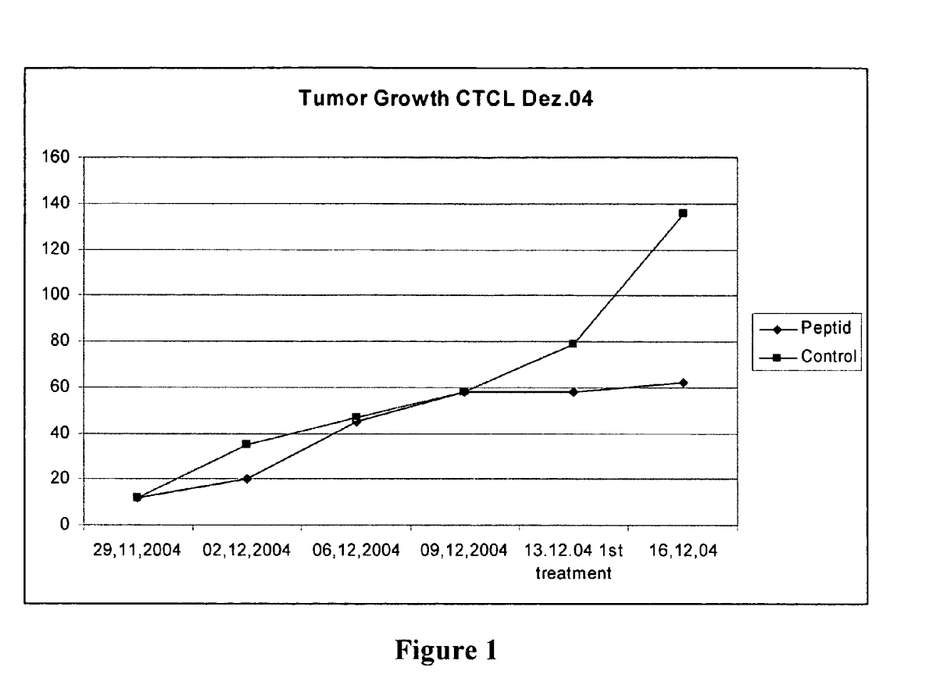
FIG. 1 shows the rate of growth of CTCL tumors using the mouse xenograft CTCL model system in mice receiving a single dose of TISF as described in Example 5.

TISF has also been tested for its effect on a cutaneous T-cell lymphoma (CTCL), using a mouse xenograft model described by T. S. Burger, et al., in *Experimental Dermatology*, vol. 13, 406-12 (2004). Cutaneous T-cell lymphomas (CTCLs) are a group of lymphoproliferative disorders involving the skin. The most common form is mycosis fungoides (MF), in which malignant growth of T-cells occurs in the form of patches and later tumors on the skin. Id. Burger, et al., discloses a method for growing human MF tumors in immune-deficient nude mice, and demonstrates that the malignant cells spread to the lymph nodes, blood stream and other organs. Using this model system, it has now been shown that TISF dramatically slows the growth of a CTCL tumor. The effect becomes apparent within days after administration of a dose of TISF, and the effect of a single dose continues for at least two weeks during the rapid growth phase of the model tumor, as shown in FIG. 1.

These data indicate that malignant cells and virus-infected cells of lymphoid or myeloid origin are induced by TISF to initiate apoptosis, and that the effect can be achieved in vivo as well as in vitro. This biological activity of TISF may usefully be applied to the treatment of a variety of disorders which are characterized by aberrant T-cells or other aberrant cells of hematopoietic origin. Such disorders include various lymphomas involving T cells, including adult T-cell lymphoma, Precursor T-cell lymphoblastic lymphoma, extranodal natural killer T-cell lymphoma, enteropathy T-cell type lymphoma, hepatosplenic T-cell lymphoma, subcutaneous panniculitis like T-cell lymphoma, mycosis fungoides or cutaneous T-cell lymphoma (CTCL), Sezary syndrome (the leukemic phase of CTCL), anaplastic large cell lymphoma, peripheral T-cell lymphoma, and angioimmunoblastic T-cell lymphoma. Additional disorders treatable by the methods and compositions described herein include certain leukemias, such as childhood leukemia of T-cell origin, adult T-cell leukemia, lymphocytic leukemia, chronic T-cell leukemia, myeloid leukemia, and erythroid leukemia. These disorders also include those viral conditions where lymphocytes are infected, and specifically HIV infection is included. TISF may benefit subjects having HIV in other ways, too, because of its immunostimulatory effects and promotion of hematopoiesis, but the present invention provides a method to induce apoptosis of the aberrant T-cells and thus reduce viral load for HIV patients.

In the case of HIV, treatment with TISF may be used to reduce the direct effects of the disease, to slow its progression, or to reduce its transmissibility, since TISF not only slows proliferation of the infected cells but also reduces production of virus. While T-cells infected with HIV are commonly killed by apoptosis caused by immune responses, it has been postulated that those T-cells harboring HIV virus that are not killed may be a critical reservoir for development of the infection. A. D. Bradley, et al., *Blood*, vol. 96(9), 2951-64 (November 2000). Thus a mechanism to kill those refractory HIV-infected cells might provide a substantial improvement to existing therapeutic protocols.

TISF or a TISF peptide may also be used in ex vivo applications. These ex vivo applications can include in vitro treatment of an aberrant T-cell, such as in a cell culture, as well as extracorporeal treatment of a tissue, cell or sample taken from a subject. The methods and compositions may, for example, be used to treat marrow samples, blood cells, or stem cell products collected for use in transplantation methods, to reduce or eliminate aberrant T-cells from such samples.

TISF may be obtained by purification from a host animal, but is alternatively obtained by purification from a thymic cell culture by methods such as those described in U.S. Pat. No. 5,616,554, which is herein incorporated by reference in its entirety. TISF is obtainable from feline, canine, ursine, equine, murine, or bovine species or from humans; in a preferred embodiment, the TISF is obtained or obtainable from the same species as the species of the subject to be treated. TISF may be used to treat aberrant T-cell conditions in canine, feline, and bovine subjects as well as in human subjects.

TISF peptides may be obtained by partial hydrolysis of or partial proteolysis of TISF using methods well known to those of ordinary skill in the art, such as methods described in D. W. Cleveland, et al., *J. Biol. Chem.* Vol. 252(3), 1102-1106 (1977) for peptide mapping. Many proteases suitable for partial digestion of peptides are known, and they can be used to partially hydrolyze TISF to produce fragments of TISF referred to herein as TISF peptides. Such fragments are within the scope of the invention provided they maintain at least 20% of the activity of a TISF as described above. Thus the term "TISF peptide" includes peptides obtained or obtainable by partial hydrolysis or partial proteolysis of a TISF from a mammalian species, provided the peptide possesses at least 20% of the biological activity of TISF, and includes TISF peptides obtained from human TISF by partial proteolysis. TISF peptides are preferably at least about 20 amino acids in length, more preferably at least about 40 amino acids in length; and they may optionally include modifications of the amino acids that correspond to those found in TISF such as glycosylations, methylations, lipidations, and the like.

TISF or a TISF peptide may be administered parenterally, intraperitoneally, topically or orally. Parenteral administration is often preferred, and intraperitoneal administration is sometimes preferred. The TISF or TISF peptide may be admixed with pharmaceutically acceptable diluents, excipients, stabilizing agents, solubilizing agents, or other pharmaceutically-indicated agents, and it may optionally be incorporated into a liposomal or slow-release matrix for administration or transdermal delivery. Typically it is delivered by injection of a pharmaceutical composition comprising TISF or a TISF peptide admixed with at least one pharmaceutically acceptable excipient.

Suitable pharmaceutical carriers and diluents, as well as pharmaceutical necessities for their use in pharmaceutical formulations, are described in *Remington's Pharmaceutical Sciences* (Alfonso Gennaro et al., eds., 17th ed., Mack Publishing Co., Easton Pa., 1985), a standard reference text in this field, in the USP/NF, and in Lachman et al. (*The Theory & Practice of Industrial Pharmacy*, 2nd ed., Lea & Febiger, Philadelphia Pa., 1976). In the case of rectal and vaginal administration, the compositions are administered using methods and carriers standardly used in administering pharmaceutical materials to these regions. For example, suppositories, creams (e.g., cocoa butter), or jellies, as well as standard vaginal applicators, droppers, syringes, or enemas may be used, as determined to be appropriate by one skilled in the art. Intravenous, intramuscular, intraperitoneal, or other types of injection administration are often advantageous, for TISF or TISF peptides; suitable compositions for such administration are well known to those skilled in the art, and appropriate excipients may be identified by reference to other polypeptide pharmaceutical compositions.

The compositions of the invention may be administered by any route clinically indicated, such as by application to the surface of mucosal membranes (including: intranasal, oral, ocular, gastrointestinal, rectal, vaginal, or genito-urinary). Alternatively, parenteral (e.g., intravenous (IV), subcutaneous, intraperitoneal, or intramuscular) modes of administration may also be used. Because TISF or a TISF peptide is a polypeptide, and is thus potentially subject to degradation upon oral or topical administration, administration by parenteral (injection) methods including intravenous delivery is often preferred. To maximize its efficient utilization, intravenous delivery of TISF or a TISF peptide is sometimes preferred and such delivery may be concurrent with delivery of other nutrient, hydration or therapeutic agents as appropriate. For intravenous administration, TISF or a TISF peptide is preferably dissolved in an aqueous or isotonic solution such as saline; phosphate buffer may be added as needed to ensure stability of the composition. Further details of compositions suitable for administration of TISF and TISF peptides are well-known to those of skill in the art by reference to other pharmaceutical compositions which contain polypeptides.

The methods of the invention typically include treatment of a subject diagnosed as in need of treatment for an aberrant activity, development or production of a T-cell or cell of hematopoietic origin, wherein the subject is treated with an effective amount of TISF or a TISF peptide. A subject can be diagnosed as in need of such treatment by one of ordinary skill, who can determine whether the subject has aberrant production, development or activity of T-cells or other hematopoietic cells using known methods to evaluate these parameters, or by diagnosing the subject by independent means as a subject having a condition known to include aberrant production, development or activity of such cells. One of ordinary skill can then determine an effective amount of TISF or a TISF peptide by monitoring the subject for improvement in response to an initial dose and determining future dosage levels according to the subject's response to the initial dose, or by using results of such treatment in similar subjects.

The amount of TISF or TISF peptide to be administered depends on the particular subject and indications, and can be determined and adjusted using routine optimization methods. Dosage may be adjusted according to the subject's size or body weight, for example, and may be based on the subject's overall health, as well as other medications or treatments administered to the subject. The mode and frequency of administration can also be determined according to the desired effect, as one skilled in the art will appreciate, and the effectiveness of the chosen regimen can readily be ascertained by monitoring the effect on the targeted hematopoietic or T-cell population, allowing the regimen to be optimized for the particular subject being treated. In general, TISF or a TISF peptide will be administered in compositions which deliver amounts of TISF or a TISF peptide ranging between about 1 µg and 500 mg per kilogram of body weight of the subject. Preferred doses are generally between about 5 µg/kg and 100 mg/kg, or between 10 µg/kg and 50 mg/kg. A dosage of 10 µg/kg to 10 mg/kg is often utilized.

Where the material is not administered in a continuous fashion such as by intravenous drip, administration may be repeated as is determined to be necessary by one skilled in the art, considering the severity of the subject's need for treatment and what other treatments the subject is receiving. In appropriate circumstances, TISF or a TISF peptide may be delivered continuously to a subject via an intravenous fluid delivery system. While a single administration of TISF or a TISF peptide has been demonstrated to produce effects lasting for several days to several weeks, repeated administration at intervals of a few hours to a month are contemplated and are within the scope of the invention. Thus TISF or a TISF peptide may be administered one to three times daily, or it may be administered one to three times per week, or one to two times per month. Determination of the dose required and the frequency of treatment required are within the ordinary skill in the art, since dosage and frequency can be adjusted until the desired effect is achieved. Progress is readily monitored by standard methods for monitoring tumor growth in CTCL, for example, or by methods for monitoring viral load in an HIV patient, for example.

Since TISF or a TISF peptide may be used to treat viral infections such as HIV and a variety of T-cell lymphomas, it is also contemplated that TISF or a TISF peptide may be admixed with or administered with other therapeutic agents appropriate for treating patients having such disorders, including but not limited to antiretroviral agents such as HIV protease inhibitors and reverse transcriptase inhibitors, radiotherapeutic treatments, and antineoplastic therapeutic agents such as alkylating agents, purine nucleoside analogs, and corticosteroids. Compositions containing a mixture of such other therapeutic agents with TISF or a TISF peptide are thus contemplated, as are treatment protocols which utilize TISF or a TISF peptide in combination with such agents. Similarly, such compositions may comprise more than one TISF and/or TISF peptide.

TISF or a TISF peptide may be administered to a subject via various means, including parenteral (especially intravenous delivery), oral, topical and intraperitoneal administration. In some cases, local delivery as by an injection or topical method may be preferred to deliver the active material to a specific location on the subject's body known to need treatment. Methods known to be useful for the administration of peptide therapeutics can be applied. The material can be delivered by suppositories or by implanted slow-release depot methods known in the art where appropriate.

A minimal effective dosage of TISF or a TISF peptide is often about 1 µg/kg of the recipient subject's body weight; preferably, at least about 5 µg per kilogram of the subject's body weight is administered to the animal, with an upper limit of about 500 mg/kg. TISF or a TISF peptide may efficaciously be administered alone or in combination with another immune potentiator, and may be incorporated in a pharmaceutically acceptable carrier or excipient. It may also be incorporated into an isotonic solution for intravenous administration.

The present invention can be better understood by way of the following examples which are representative of certain preferred embodiments thereof, but which are not to be construed as limiting the scope of the invention.

EXAMPLES

Example 1

Lymphoma cells were incubated for 48 hr in the presence of TISF at several different concentrations. The cells were then treated with $^3$H-thymidine to measure cell proliferation. At each concentration, TISF inhibited cell growth. As a control to determine whether the effect was a general cytotoxicity, a non-lymphoid malignant cell line was also treated with TISF, and TISF had no effect on the rate of growth in that case.

Example 2

Lymphocytes infected with the HIV virus were incubated with TISF at different doses. Cell death occurred at each concentration tested, and the extent was dose-dependent. Moreover, the concentration of TISF correlated with decreased production of virus.

Example 3

The human myelomonocytic leukemia cell line K562 was incubated with TISF. The rate of apoptosis increased more than two-fold over that in a control culture.

Example 4

TISF may be obtained by the following procedures from U.S. Pat. No. 5,616,554.

A cloned cell line of thymic cells may be established as described herein. For example, in accordance with the present invention, thymic stromal cells of feline origin were established as a continuously replicating, cloned cell line, according to the method described in Beardsley, et al., PNAS 80:6005 (1983), which is incorporated herein by reference. A selection process was used to isolate a cell line producing homogenous TISF.

The same technique has been employed to establish cloned thymic epithelial cell lines from thymic tissue removed from juvenile dogs and calves and from human thymic remnants removed from children undergoing cardiac surgery.

Preparation of Thymic Cell Lines: Briefly, the procedure for reproducibly obtaining the cell lines of the present invention is as follows. Thymus tissue was removed aseptically under general anesthesia. The tissue removed was placed immediately into tissue culture. A primary culture of about $1 \times 10^8$ thymocytes was established in a 60 mm Petri dish in 5 ml of DMEM and 20% fetal calf serum. After about 48 hours, the thymocytes were gently washed away and the scattered few adherent cells were fed with 50% fresh DMEM containing 20% fetal calf serum and 50% conditioned medium, obtained after centrifugation of the thymocytes. Primary cultures containing a variety of cell types were maintained by weekly feeding with a similar 50:50 mixture of fresh and conditioned medium. After about four weeks, several isolated colonies of epithelial-like cells covered the plate. At this time, a secondary culture was made by transfer of several of these colonies scraped from the primary culture. Growth tended to be slow until the third subculture, when cells began to form a monolayer within 4-5 days. Cloning of the cells by limiting dilution at one cell per well was less successful than "seeding" the wells with three or four individual cells, which tended to grow to confluency. Single cells plated in limiting dilution were more likely to grow to confluency if epidermal growth factor was added at 6 ng/ml to wells containing single cells.

Clones exhibiting epithelial-like morphology were grown out and the supernatants tested for their ability to enhance alloreactivity in whole thymocyte populations. Supernatants from confluent thymus-derived cultures were tested for their capacity to promote thymocyte functional activity. For example, one such method involved testing the ability of the supernatant to augment the cytotoxic T lymphocyte (CTL) response of thymocytes to allogenic major histocompatibility complex (MHC) antigen. Supernatants exhibiting the capacity to induce or enhance cell-mediated immune responsiveness were preferentially selected for testing and further purification.

Cells are preferably propagated in Dulbecco's minimal essential medium (DMEM) high glucose formulation (Irvine Scientific, Santa Ana, Calif.), supplemented with L-glutamine and one or more appropriate antibiotics (i.e., penicillin G 100 IU/ml; streptomycin 100 μg/ml). The medium may further be supplemented with 1-10% fetal bovine serum or proven serum-free substitute (e.g. Serxtend™, Irvine Scientific, Santa Ana, Calif.). Maintenance medium is made as noted above, without the serum.

The cell cultures may be propagated and maintained according to known methods. Those used in the present invention were propagated in an artificial capillary bed (hollow fiber bioreactor) according to the method described in Knazek and Gullino, *Tissue Culture Methods and Applications*, Chapt. 7, p. 321 et seq., Kruse and Patterson, eds., Academic Press, N.Y., 1973, which is incorporated herein by reference. Another means of propagating and maintaining a cell line is via weekly passage and growth in DMEM and 10% fetal calf serum. The growth medium may be removed from 5-day cultures and replaced with serum-free DMEM for 24 hours. The 24-hour supernatant is useful as the source of thymic factor. A cloned feline cell line in accordance with the present invention is permanently maintained by the inventor under the designation Fe2F, a canine cell line is permanently maintained under the designation Ca-9, a bovine cell line is permanently maintained under the designation TF4, and a human cell line is permanently maintained under the designation HU1.

In a preferred embodiment, as illustrated by the following examples, thymic stromal cell-derived TISF is produced by type II epithelial cells. Cloned cells from a primary culture of thymic tissue are selected initially on the basis of morphology (see Beardsley, et al., *PNAS* 80:6005 (1983)), for example, for a description of desired morphological characteristics). Secondarily, cloned lines are selected on the basis of production of TISF, as determined by known in vivo or in vitro bioassay procedures. Purity of the cultures is maintained via regular monitoring for invasive organisms including viruses, bacteria, and fungi.

Purification of Thymic Factor: TISF is a strongly cationic glycoprotein, and may be purified with cation exchange resin. Purification of the supernatants selected produced a substantially homogeneous factor (TISF). Using known assay techniques as described above, it is now apparent that the effective component of TISF is comprised of at least one polypeptide substantially free of additional endogenous materials. The human, feline, canine and bovine TISF of the present invention are substantially homogeneous 50 kDa glycoproteins with isoelectric points of 6.5.

The amino acid composition of TISF is unlike that of any known cytokine or thymic peptide. The amino acid composition of bovine TISF was determined by conventional methods known to those of skill in the art and is as follows.

Asparagine/Aspartate—8.8%; Threonine—3.5%; Serine—14.7%; Glutamine/Glutamate—13.3%; Proline—2.2%; Glycine—25.7%; Alanine—6.1%; Valine—4.3%; Isoleucine—3.4%; Leucine—6.3%; Tyrosine—2.3%; Phenylalanine—2.6%; Histidine—2.2%; Lysine—4.7%

TISF was purified on a larger scale according to the following protocol. Seed cultures of Fe2F, Ca-9, TF4, or HU 1 were removed from frozen culture and grown in 25 $Cm^2$ tissue culture dishes in supplemented DMEM. After 14-21 days incubation at 36° C., cultures were used to inoculate a hollow fiber bioreactor. $5 \times 10^6$-$10^8$ cells were inoculated into the extracapillary space (ECS) of an artificial capillary bed. One liter of DMEM supplemented with L-glutamine and antibiotics (e.g., penicillin G, 100 U/ml or streptomycin, 100 μg/ml) was circulated in the capillary bed.

After seeding the reactor and allowing for adaptation (3-6 weeks), the concentration of fetal bovine serum was gradually decreased to approximately 0.5% in the media. Cultures were fed every other day by replacement of the circulating capillary bed media. Product was harvested from the media removed from the ECS of the reactor. In one procedure, for example, 500-1000 ml media was exchanged in the capillary bed and 30 ml in the ECS.

When one liter of ECS fluid was collected, it was clarified by centrifugation. The clarified material was passed through a sterile chromatography column which contained a strong cation exchange resin (Sepharose S, Pharmacia) with a high affinity for the product at low salt concentrations. The column was eluted with increasing salt concentrations to 0.5M, whereby all extraneous material was removed from the column. The strongly cationic product was then eluted with sterile 2M buffered saline. The material was then diluted with sterile water to the concentration of normal saline. The final product has a preferable concentration of about 1 μg/ml. The product may be lyophilized, if desired, for long term storage.

Example 5

Figure 4:
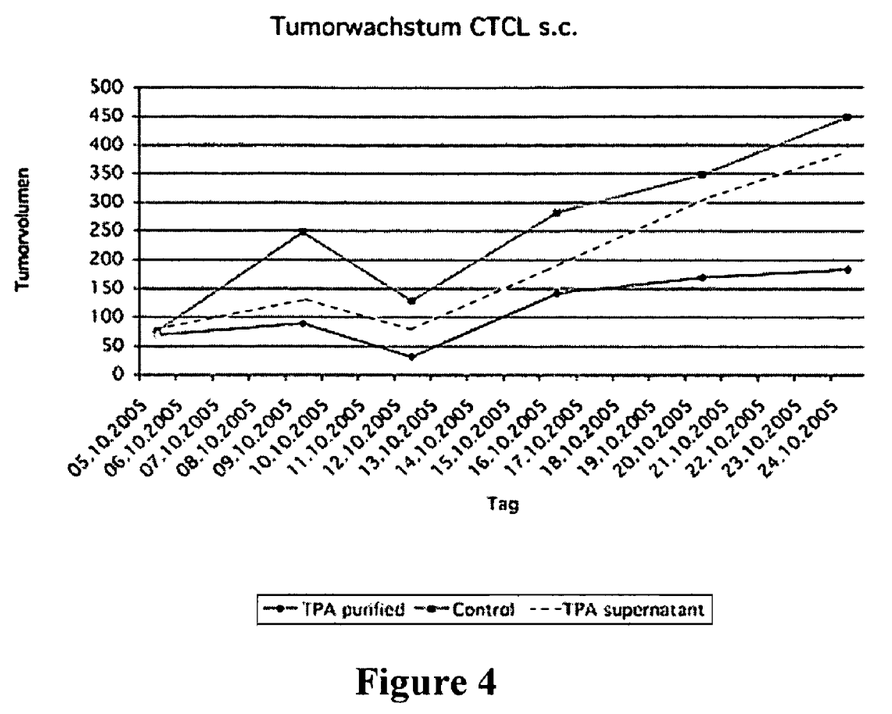
FIG. 4 shows the rate of tumor growth (Tumor volume) for CTCL tumors in the mouse xenograft model, using the supernatant from a TISF producing cell culture ("TPA supernatant") and using a partially purified sample of TISF ("TPA purified"), demonstrating that the cell culture supernatant has a tumor growth-suppression effect, while the purified TISF composition has a much greater growth-suppression effect. The tests were performed according to Example 5, and the dates indicate when tumor volume was assessed following an initial treatment with TISF or the supernatant.
Figure 5:
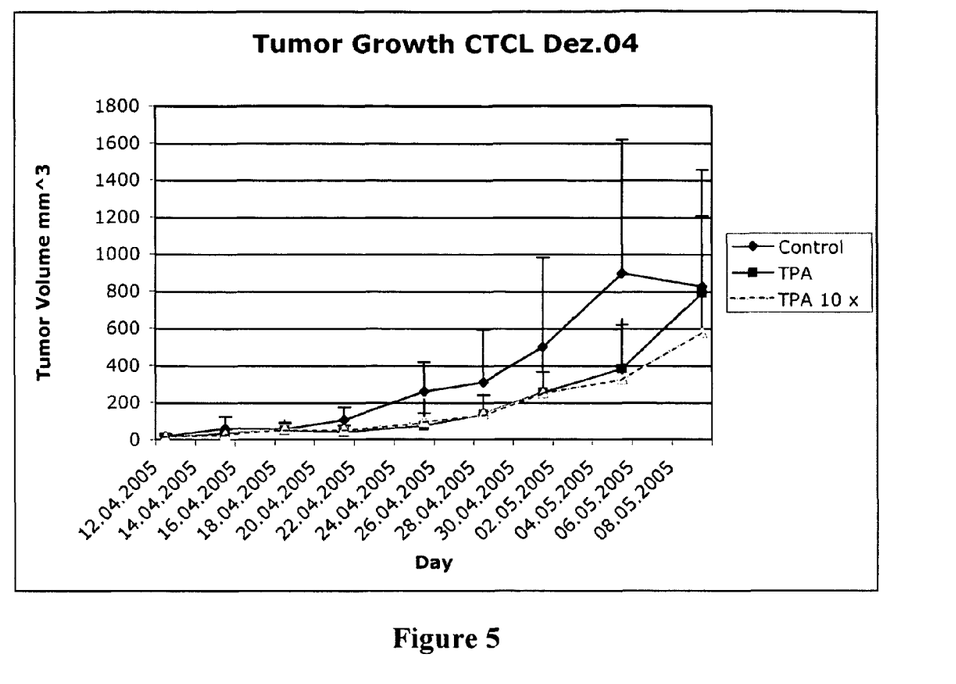
FIG. 5 shows the rate of tumor growth (Tumor volume) for CTCL tumors in the mouse xenograft model using a composition containing a partially purified TISF (identified as TPA) at two different concentrations: "TPA 10×" (the dashed line) represents a ten-fold higher TISF concentration than TPA (squares). Both concentrations have an effect on tumor growth for at least several weeks after administration of TISF, and the response is dose dependent. The tests were performed according to Example 5, and the dates indicate when tumor volume was assessed following an initial treatment with TISF.
Figure 6:
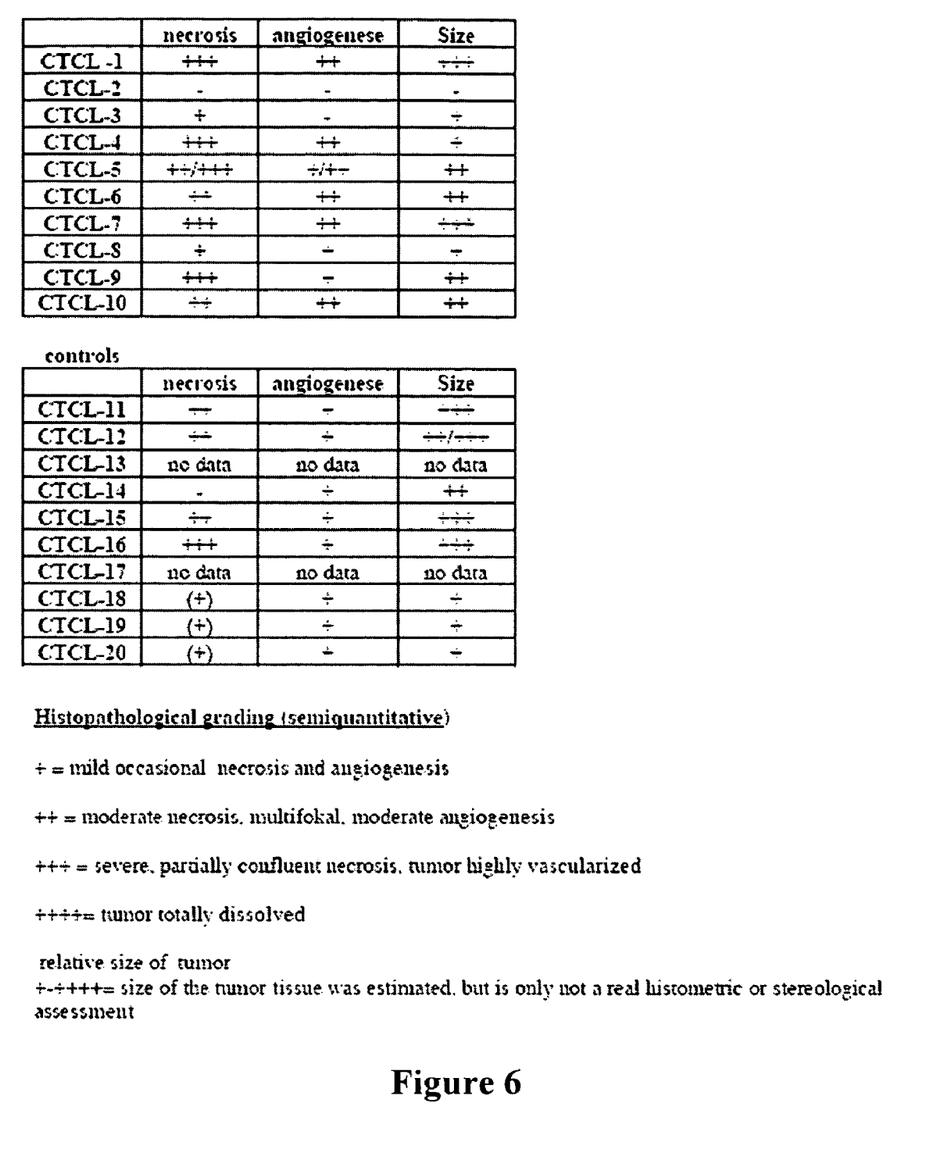
FIG. 6 summarizes the histological examination of each of the mice used in the experiment described in Example 6.
Figure 7:
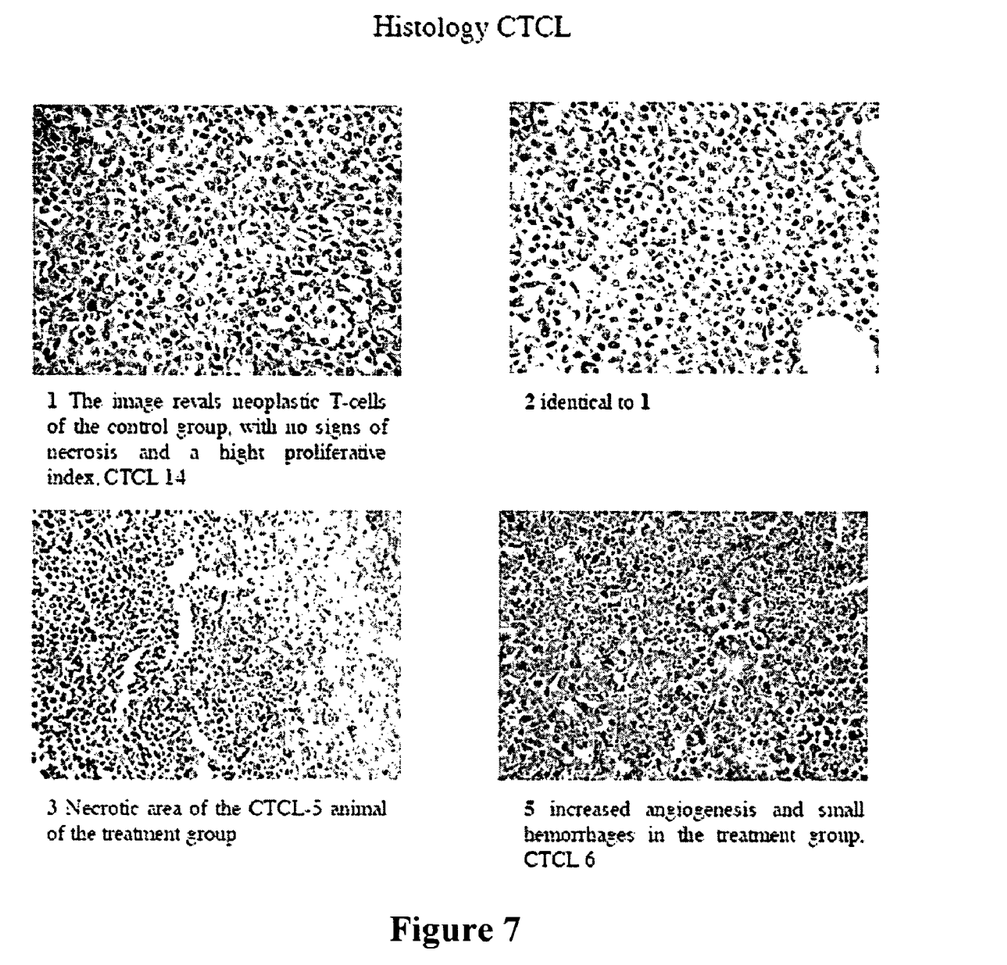
FIG. 7 shows histological images of tumor tissue from representative mice from the experiment described in Example 6.

Model cutaneous T-cell lymphoma (CTCL) tumors were established in mice by the method described in T. S. Burger, et al., *Establishment of a mouse xenograft model for mycosis fungoides*, Experimental Dermatology, 13, 406-412 (2004). Approximately 14 days after implanting tumor cells, the mice were treated with TISF. Tumor volume in $mm^3$ was evaluated according to Burger, et al., as Size=length×(width)$^2$×0.5. At about the time of the treatment, the tumor growth rate increased sharply in untreated mice, while the single dose of TISF significantly suppressed the tumor growth rate in treated animals. The results are summarized in FIGS. 1, 4 and 5. FIG. 1 shows that tumor volume was over twice as large in untreated mice as in treated mice three days after treatment. FIG. 4 shows that a strong effect from a single dose is maintained at least 19 days after a single treatment, and that the effect is much stronger when a purified TISF composition is used. FIG. 5 illustrates that the effect of TISF is dose-dependent.

Example 6

Six-week old NMRI nude mice were obtained from Harlan Winkelmann, Borchen, Germany, and were maintained in individual ventilated cages, food and water ad libitum. CTCL tumor tissue was implanted under anesthesia in the flank of the animals on Nov. 24, 2004, and tumor size was monitored twice weekly using the methods described in *Experimental Dermatology*, 13, 406-412 (2004). Groups of 10 animals were used for a treatment group and a control group.

The treatment group animals were treated with 100 μL injections of reconstituted TISF solution; the control group animals were injected with 100 μL of dilute saline solution. Treatments were administered daily as follows: Dec. 13-17, 2004; Dec. 20-24, 2004; Dec. 27-31, 2004; and Jan. 3-5, 2005. The animals were sacrificed on Jan. 6, 2005.

Figure 2:
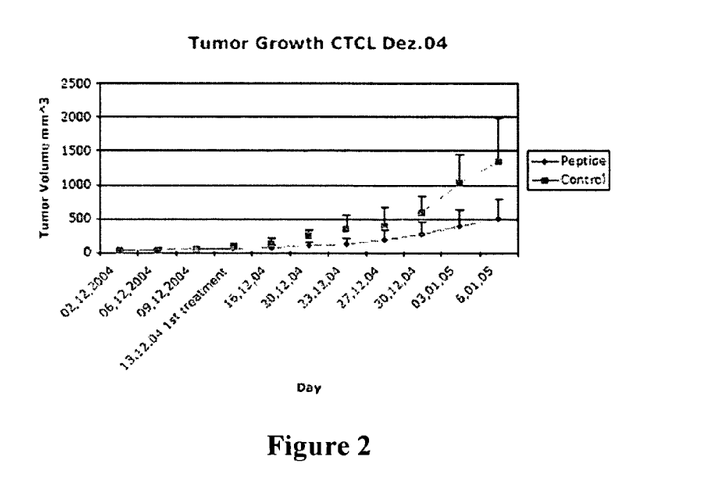
FIG. 2 shows the rate of growth of CTCL tumors using the mouse xenograft CTCL model system. The squares represent an untreated control, while the diamonds represent growth rate of tumors in mice receiving several doses of TISF per week as described in Example 6.
Figure 3:
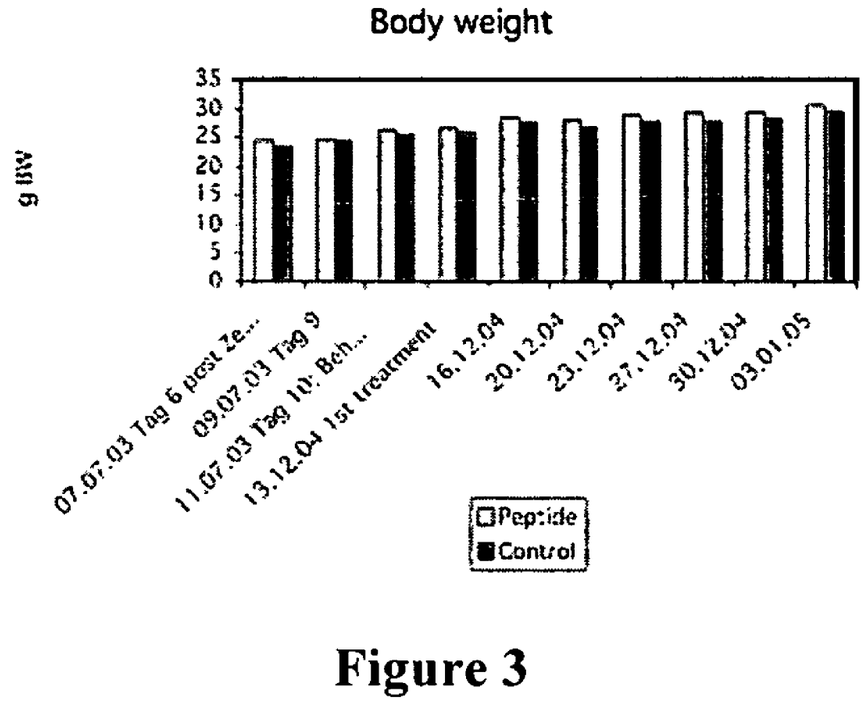
FIG. 3 shows the body weight for the control and treated mice from Example 6.

When treatments began, the tumor volume was approximately 80 mm$^3$. FIG. 2 shows the rate of tumor growth in the control group (represented by square data points) and the treated group (represented by diamond-shaped data points), and demonstrates that the treatment slowed tumor growth substantially. When the animals were sacrificed, tumor volume was nearly three times larger in the untreated (control) animals when compared to the treated animals. FIG. 3 shows the body weights of the animals, and indicates that treatment with TISF had no significant effect on the overall growth rate of the treated animals.

Tissue from the tumors was stained with hematoxylin and eosin for histological examination. Tumor tissue from the treated animals demonstrated a slight increase in coagulative necrosis and a slight increase in angiogenesis relative to the controls. FIG. 4 shows the results of the histological examination of each animal, and FIG. 5 shows representative images of the tumor tissue from treated and untreated animals.

Example 7

Cytotoxicity was measured using a standard MTT assay protocol. MyLa cells were seeded in 96-well plates and TISF, diluted with cell culture medium, was added. Cells were incubated for 16 hours, and cell growth inhibition was measured by standard methods.

| TISF Dilution (reconstituted peptide:medium) | % Inhibition of Cell Growth |
| --- | --- |
| 4:100 | 40% |
| 2:100 | 52% |
| 1:100 | 54% |
| 0.5:100 | 52% |
| 0.25:100 | 35% |
| 0.12:100 | 44% |
| 0.07:100 | 17% |
| 0.03:100 | 11% |

The foregoing examples are intended to better explain certain aspects and embodiments of the present invention, and are not intended to define its scope or imply limitations thereon.

The invention claimed is:

1. A method to treat a subject diagnosed as having a disorder characterized by aberrant T-cell production, development, or activity, which method comprises administering to the subject an effective amount of TISF having a molecular weight of about 50,000 Daltons, wherein the disorder is cutaneous T-cell lymphoma.

2. The method of claim 1, wherein the subject is treated with an effective amount of TISF, and wherein the TISF is obtainable from a mammalian species.

3. The method of claim 1, wherein the subject is treated with an effective amount of TISF, and wherein the TISF is obtained from a mammalian cell culture.

4. The method of claim 1, wherein the cutaneous T-cell lymphoma is mycosis fungoides.

5. The method of claim 2, wherein the cutaneous T-cell lymphoma is mycosis fungoides.

6. The method of claim 3, wherein the cutaneous T-cell lymphoma is mycosis fungoides.

* * * * *